United States Patent [19]

Reinicke

[11] 4,197,835

[45] Apr. 15, 1980

[54] PROSTHETIC URINARY SPHINCTER CONTROL DEVICE

[75] Inventor: Robert H. Reinicke, Mission Viejo, Calif.

[73] Assignee: Parker-Hannifin Corporation, Cleveland, Ohio

[21] Appl. No.: 884,863

[22] Filed: Mar. 9, 1978

[51] Int. Cl.² ........................ A61B 17/00; A61F 1/00
[52] U.S. Cl. .................................... 128/1 R; 60/591; 92/92; 128/346; 128/DIG. 25
[58] Field of Search ............... 128/1 R, 346, DIG. 25; 3/1; 60/533, 591; 92/92

[56] References Cited

U.S. PATENT DOCUMENTS

| | | | |
|---|---|---|---|
| 2,455,859 | 12/1948 | Foley | 128/346 |
| 3,744,063 | 7/1973 | McWhorter et al. | 128/1 R |
| 4,056,095 | 11/1977 | Rey et al. | 128/1 R |

FOREIGN PATENT DOCUMENTS 1174814  12/1969  United Kingdom ............ 128/DIG. 25

Primary Examiner—Dalton L. Truluck
Attorney, Agent, or Firm—John N. Wolfram

[57] ABSTRACT

A device for controlling flow of fluid to and from a resilient inflatable cuff implanted about the urethra to control flow of urine therethrough. The device comprises a housing of rigid material that provides an expansible sealed chamber, a piston forming one wall of the chamber and spring pressed to a position for decreasing the volume of the chamber to thereby force fluid from the chamber to the cuff, manually operable means for moving the piston to another position for enlarging the chamber to permit deflation of the cuff by return of fluid to the chamber, and a flexible cover or envelope encapsulating the housing, piston and manually operated means.

10 Claims, 4 Drawing Figures

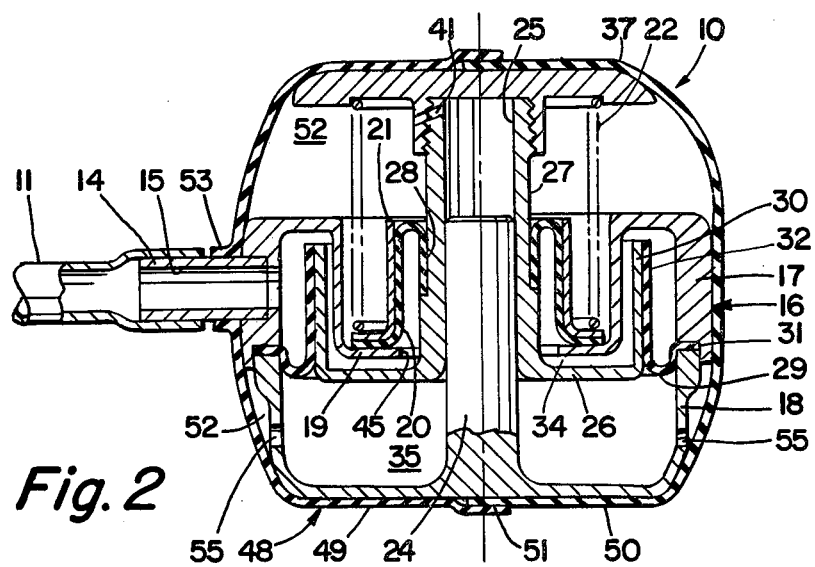
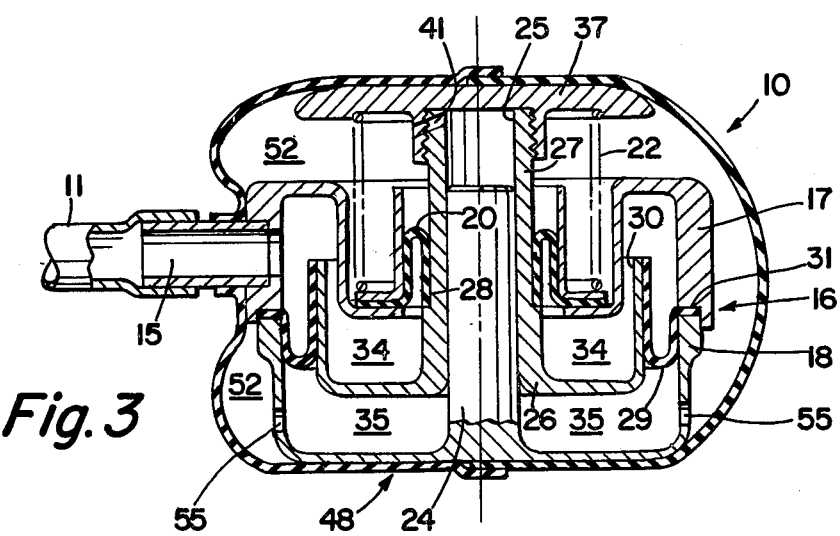
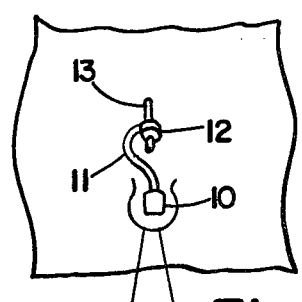
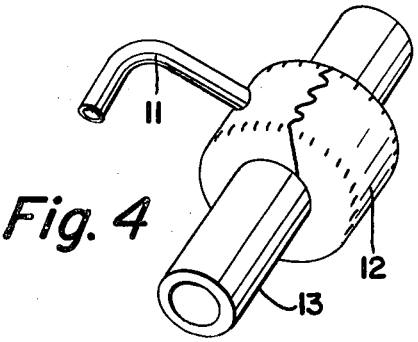

PROSTHETIC URINARY SPHINCTER CONTROL DEVICE

BACKGROUND OF THE INVENTION

For various reasons some persons lose control of the sphincter muscle that opens and closes the urethra leading from the bladder whereby urinary incontinence results. In the past various devices has been proposed for implantation in the human body for remedying this condition. Such devices are shown for example in U.S. Pat. Nos. 3,744,063, 3,863,622, 3,854,469, 3,903,894, and 4,019,499. They include a resilient inflatable cuff or other member that surrounds the urethra and which when inflated squeezes the urethra closed and when deflated permits it to be open. In some cases such prior devices have included valves for controlling the flow of fluids to and from the inflatable member and consequently may be subject to malfunction in the event a valve fails to open or close properly. In other cases the prior devices contain the actuating liquid in a bulb of flexible material that is subject to unlimited manually applied pressure that may cause excessive pressure on the actuating liquid with damage to or rupture of the parts.

SUMMARY OF THE INVENTION

In the present invention the device for storing actuating liquid and for causing inflation and deflation of a cuff for opening and closing the urethra is valveless and consequently eliminates all problems that malfunctioning valves entail. The device is of simple construction and of small size so that both implantation in the human body and manual operation by the person in whom implanted are facilitated.

The device comprises a housing of rigid material that encloses a piston that forms a sealed expansible chamber with a portion of the housing. The chamber has a port for connection to a tube leading to the cuff. A spring holds the piston in a position in which the chamber size is small and liquid has been displaced therefrom into the cuff to inflate the latter for normally maintaining the urethra closed. A manually operated actuator is connected to the piston so that by manual manipulation of the actuator the piston may be moved to enlarge the chamber to permit return of liquid to the chamber from the cuff to deflate the cuff and permit opening of the urethra. The rigid housing completely surrounds the piston and provides a stop for the same to prevent excessive travel of the piston upon application of excessive manual pressure. All the parts of the device are enclosed in a cover or envelope of flexible sheet material to prevent contact of such parts with human tissue. The envelope is completely filled with liquid so that no air pockets are contained in the device.

BRIEF DESCRIPTION OF THE DRAWINGS

FIG. 1 illustrates the device as connected to an inflatable cuff and implanted in the human body.

FIG. 2 is a cross-section view of the device in its normal position in which the urethra is closed.

FIG. 3 is a view like FIG. 2 showing the device in its actuated position for opening the urethra.

FIG. 4 is a view of the cuff in position on the urethra.

DETAILED DESCRIPTION

As shown in FIG. 1, the device 10 of the present invention is connected by a tube 11 to an inflatable cuff 12. All these parts are implanted surgically into a human body. Cuff 12 is a hollow donut shaped member of resilient flexible material such as a silicone elastomer and is implanted in the body so that it surrounds the urethra 13. Device 10 is preferably implanted within the scrotum of male patients where it is readily accessible for digital manipulation or it may be implanted at other locations in the male or female body where it may be actuated by externally applied pressure.

Device 10 has a housing 16 that comprises two members 17 and 18 of relatively rigid material such as stainless steel. Housing member 17 has a ledge 19 against which a rolling type diaphragm 20 is clamped by a guide sleeve 21 and a spring 22 and also has a tubular extension 14 with an opening 15. Housing member 18 has a central stem 24 which is a slide fit within bore 25 of a piston 26 having a central tubular portion 27. Diaphragm 20 is sealingly attached at 28 to piston tubular portion 27, preferably by cementing, and there is another diaphragm 29 sealingly attached to a tubular flange 32 of piston 26 at 30 and which is sealingly clamped at 31 between housing parts 17 and 18.

Piston 26 divides the interior of housing 16 into an expansible chamber 34 for containing a liquid and a second chamber 35 to accommodate movement of piston 26. Attached to piston 26 is a actuator button 37 against which one end of spring 22 bears. All the parts of device 10 thus far described are contained within a cover or envelope 48 of flexible sheet material and comprising two members 49, 50 cemented together at 51.

A bleed passage 41 through portions of button 37 and piston portion 27 connects piston bore 25 with the interior 52 of envelope 48 and ports 55 in member 18 connect the interior 52 of envelope 48 with chamber 35. Envelope member 49 has a tubular section 53 through which tubular portion 14 extends and is cemented thereto. Before implantation of the complete unit in a person's body, an actuating liquid, such as a saline solution, is introduced into chamber 34 while piston 26 is in the position of FIG. 3 and into chamber 35, bore 25 and the interior 52 of envelope 48 to completely fill the latter so that air is completely excluded from the device. The liquid in chamber 34 communicates only with tube 11 and cuff 12 and is sealed from the remaining fluid within cover 48. Tube 11 is then sealingly connected to cuff 12 and tubular extension 14. Diaphragms 20, 29 and envelope 48 may be of silicone elastomer or other suitable flexible sheet material.

OPERATION

When cuff 12, device 10 and connecting tube 11 have been implanted as described, spring 22 maintains piston 31 in the position shown in FIG. 2 wherein liquid from sealed chamber 34 has been forced through tube 11 to cuff 12 to inflate the latter and cause it to close urethra 13. There is sufficient liquid in this portion of the system so that piston 26 will not be bottomed on housing 16 and the pressure on the liquid in cuff 12 will depend directly upon the spring force.

To permit opening of urethra 13, external pressure, such as by digital manipulation, is applied to acutator button 37 to move piston 26 against the pressure of spring 22 to the position shown in FIG. 3. In this position chamber 34 has been enlarged and liquid has been transferred thereto from cuff 12 to deflate the latter to permit urethra 13 to open. Transfer of liquid from the cuff to chamber 34 is caused both by the return of the material of the cuff to its deflated condition and by the tendency of a vacuum to form in chamber 34 as it becomes enlarged. Movement of piston 26 for enlarging chamber 34 may be positively limited either by engagement of the lower portion of piston 26 with housing member 18 or by engagement of button 37 with member 17.

As piston 26 moves to the position of FIG. 3, it displaces liquid from chamber 35 through openings 55 into cover or envelope 48 whereby piston 26 moves with little resistance from liquid in chamber 35. Likewise, liquid in piston bore 25 is displaced through port 41 into the interior 52 of envelope 48 to prevent hydraulic lock in bore 25.

Upon release of digital pressure on button 37, spring 22 returns the button and piston 26 to the position of FIG. 2, causing liquid in chamber 34 to be expelled through opening 15 and tube 11 into cuff 12 to again inflate the latter and cause the urethra to be closed. At the same time liquid passes from the interior of cover 48 through openings 55 into chamber 35 to avoid drawing of a vacuum in such chamber that might otherwise prevent full stroking of piston 26 and full inflation of the cuff.

We claim:

1. A device for controlling flow of fluid to and from a prosthetic urinary sphincter cuff, said device comprising a housing of rigid material, a piston of rigid material within the housing and movable relative thereto, said rigid piston and rigid housing defining a variable volume chamber for receiving fluid, said piston including a portion extending through said rigid housing and through said variable volume chamber, said piston portion including a bore, said housing including a stem slidably disposed in said bore and defining and guiding the movement of said piston relative to said housing, resilient means urging the piston toward a position for decreasing the volume of the chamber, a port connected to the chamber and through which fluid may pass to or from the chamber, and said piston having a means by which it may be moved to a position for increasing the volume of said chamber.

2. The device of claim 1 in which said housing and piston form a second variable volume chamber, said resilient means urges said piston toward a position for increasing the volume of said second chamber, and said second chamber is vented to the exterior of the housing through a vent port.

3. The device of claim 2 including a leakproof flexible elastomeric envelope totally encapsulating said housing and said piston and said first and second chambers and said ports, and said envelope is substantially filled with a liquid.

4. The device of claim 1 in which there is a stop means for positively limiting the travel of the piston in the direction for increasing the volume of the chamber, and the stop means comprises engageable surfaces on the piston and housing.

5. The device of claim 1 in which said means for moving the piston is on said portions of said piston.

6. A device for controlling flow of fluid to and from a prosthetic urinary sphincter cuff, said device having a housing, a movable piston sealed relative to the housing to form therewith a first variable volume chamber, a spring normally urging the piston to a position for decreasing the volume of the first chamber, manually operable means for moving the piston to a position for increasing the volume of the first chamber, a port connecting the interior of the first chamber to the exterior thereof and through which fluid may pass to and from the first chamber, said housing and piston defining a second variable volume chamber, said spring urging said piston toward a position for increasing the volume of said second chamber, said second chamber being vented to the exterior of said housing through a vent port, a leakproof flexible elastomeric envelope totally encapsulating said housing and said piston and said first and second chambers and said ports, and said envelope being substantially filled with a liquid.

7. The device of claim 6 in which said first mentioned port is formed in a tubular member that projects through said envelope to the exterior thereof.

8. The device of claim 6 in which the piston has a portion that projects from said chamber, said manually operable means is carried by said portion and said spring is exterior of said housing and engages the housing and the manually operable means.

9. The device of claim 6 in which the piston is of rigid material and is sealingly connected to the housing by a flexible diaphragm.

10. The device of claim 8 in which said portion is sealed relative to the housing by a flexible diaphragm.

* * * * *